US005855906A

United States Patent [19]
McClay

[11] Patent Number: 5,855,906
[45] Date of Patent: Jan. 5, 1999

[54] INTRAVAGINAL DRUG DELIVERY DEVICES FOR THE ADMINISTRATION OF 17β-OESTRADIOL PRECURSORS

[75] Inventor: Allen McClay, Cookstown, Ireland

[73] Assignee: Galen (Chemicals) Limited, Dublin, Ireland

[21] Appl. No.: 849,329

[22] PCT Filed: Dec. 19, 1995

[86] PCT No.: PCT/IE95/00063

§ 371 Date: Jun. 3, 1997

§ 102(e) Date: Jun. 3, 1997

[87] PCT Pub. No.: WO96/19196

PCT Pub. Date: Jun. 27, 1996

[30] Foreign Application Priority Data

Dec. 19, 1994 [IE] Ireland .................................. S940976
Apr. 5, 1995 [IE] Ireland .................................. S950247

[51] Int. Cl.$^6$ ...................................................... A61F 13/00
[52] U.S. Cl. ............................ 424/433; 424/430; 424/422
[58] Field of Search ...................................... 424/433, 430, 424/422

[56] References Cited

U.S. PATENT DOCUMENTS 3,545,439 12/1970 Duncan .................................... 128/260
4,291,014 9/1981 Keith .......................................... 424/28

Primary Examiner—D. Gabrielle Brouillette
Attorney, Agent, or Firm—Jay H. Maioli

[57] ABSTRACT

The invention relates to an intravaginal drug delivery device for administration to a female mammal of certain 17β-oestradiol precursors at a substantially constant rate for a period of at least three weeks. The 17β-oestradiol precursor is a 17β-oestradiol moiety in which the, or each, hydroxyl group of the 17β-oestradiol moiety is blocked by a blocking group, which blocking group is readily removed from the 17β-oestradiol in vivo. The 17β-oestradiol precursor must have either a solubility in liquid silicone of not less than 0.1 mg/100 ml or a standard k value of not less than 0.1 μg/day/mm. The 17β-oestradiol precursor must also have a solubility in distilled water of not less than 1 μg/100 ml.

24 Claims, 2 Drawing Sheets

INTRAVAGINAL DRUG DELIVERY DEVICES FOR THE ADMINISTRATION OF 17β-OESTRADIOL PRECURSORS

This application is a 371 of PCT/IE/00063, filed Dec. 12, 1995.

This invention relates to intravaginal drug delivery devices for the administration of 17β-oestradiol precursors. The term "17β-oestradiol precursor" is intended to embrace certain compounds which can be converted into 17β-oestradiol, which compounds possess physicochemical and clinical properties as defined hereinbelow. In particular, the present invention relates to intravaginal drug delivery devices for the administration of a 17β-oestradiol precursor at a substantially constant rate over a prolonged period for oestrogen-requiring conditions such that either the symptoms associated with hypo-oestrogenism may be alleviated or prevented or, alternatively, fertility is controlled. More particularly, the invention relates to, but is not limited to, an intravaginal drug delivery device for the administration of a 17β-oestradiol precursor for hormone replacement therapy in the human female.

Hypo-oestrogenism in the premenopausal human female may occur due to disease, oophorectomy or traumatic injury [2]. In the postmenopausal human female, hypo-oestrogenism occurs as a natural consequence of the ageing process. Fertility control involves the administration of sufficient oestrogen to prevent ovulation, in effect, an induced hyper-oestrogenism. The description hereinafter primarily concerns the utility of intravaginal drug delivery devices of the invention for the alleviation or prevention of symptoms associated with hypo-oestrogenism, specifically, hormone replacement therapy, but it will be appreciated that the intravaginal drug delivery devices of the invention may also be used to induce hyper-oestrogenism, specifically, to prevent ovulation and, therefore, to act as a contraceptive.

In the normal, healthy human female, 17β-oestradiol is the principal oestrogen produced by the functioning pre-menopausal ovary, primarily in the ovulating follicle, during each menstrual cycle [1]. Circulating 17β-oestradiol levels vary during the monthly cycle in the premenopausal human female, being at their highest during the peri-ovulatory phase (about 1000 pmol per liter). As ageing progresses in the human female, ovulation becomes less frequent and less predictable, resulting in diminished production of 17β-oestradiol. At the menopause, when irreversible failure of ovarian follicular activity occurs, 17β-oestradiol production decreases dramatically to less than 20 μg per day, giving circulating levels of 17β-oestradiol in serum of less than 30 pg/ml [2] (1 pg/ml is equivalent to 3.676 pmol/l, assuming a molecular weight of 272 for oestradiol)

Non-oral 17β-oestradiol preparations intended for use in hormone replacement therapy typically deliver plasma levels of 17β-oestradiol corresponding to mean levels of the hormone in the premenopausal subject at days 6 to 8 (about 200 pmol per liter) and days 8 to 10 (about 360 pmol per liter) of the cycle. For the transdermal route, which is one non-oral route, these plasma concentrations correspond to a dose of 50 μg per day (low dose) to 100 μg per day (high dose). This is generally accepted as the desirable non-oral dosage range in order to provide efficaceous relief of post-menopausal symptoms whilst minimising potential toxicity [1].

Hypo-oestrogenic (including postmenopausal) symptoms may be classified [3] as:

(a) Neuroendocrine symptoms, characterised by one or more of the following: hot flushes, night sweats, insomnia, mood changes, anxiety, irritability, loss of memory and loss of concentration.

(b) Lower urinogenital tract symptoms, characterised by one or more of the following: genital tract atrophy, dyspareunia, loss of libido, urethral syndrome.

(c) Miscellaneous symptoms, characterised by one or more of the following: joint aches, paraesthesia, dry skin, dry or brittle hair, brittle nails.

In those cases where the combination of symptoms is sufficiently severe, it is well recognised that oestrogen hormone replacement therapy is indicated. In the postmenopausal human female requiring such therapy, the aim is to restore premenopausal oestrogen balance by delivering the natural oestrogenic hormone, 17β-oestradiol, to the systemic circulation in a pattern that mimics its physiological secretion, that is, continuously and at a low but effectively constant rate [4]. It is well recognised by practitioners that hormone replacement therapy, once initiated in the human female, may be necessary for many years extending from the onset of the menopause. A physiologically effective dose of 17β-oestradiol, sufficient to provide effective control of all postmenopausal symptoms, is considered to be at least 50 μg per day [1], although transdermal patches delivering as low as 25 μg per day will elevate plasma oestradiol levels and are used in oestrogen replacement therapy.

Oral administration of oestrogen, including 17β-oestradiol, for hormone replacement therapy has a number of disadvantages [1,5]:

(a) Oral administration of a drug is followed, primarily, by absorption through the gastrointestinal tract, from where the blood flow is to the liver. Some 60–90% of orally administered drug will be metabolised during this first pass through the liver. As a result, oral oestrogen therapy results in oestrone, a less potent oestrogen, as the predominant circulating oestrogen.

(b) Oral therapy involves bolus doses resulting in high initial oestrogen levels which are non-physiological, a non-steady state of circulating serum oestrogen and a non-physiological 17β-oestradiol:oestrone ratio.

Given the long-term nature of hormone replacement therapy, a drug delivery system that promotes improved patient compliance and convenience by reducing the dosing frequency or by requiring less frequent dosing is desirable. Various routes of oestrogen administration have been suggested, including transdermal, subcutaneous and intravaginal administration:

Oestrogens are efficiently absorbed by the transdermal route. First pass effects are avoided and a physiological 17β-oestradiol:oestrone ratio is maintained. Transdermal administration of 17β-oestradiol is, therefore, preferable to the oral route [4]. Patient compliance and convenience are also enhanced. However, the physical size of the transdermal drug delivery system is such that a new device must be used every few days. This can lead to fluctuations in circulating serum oestrogen levels, which is inconvenient and has possible compliance problems for the patient.

Subcutaneous implantation of 17β-oestradiol-loaded pellets provides therapy extending to several months and is therefore advantageous in respect of both patient compliance and convenience. However, subcutaneous implants have a number of disadvantages [2]:

(a) A surgical procedure is required for insertion of the pellets.

(b) Infection can arise at the insertion site.

(c) The pellets are difficult to remove in the event of a problem developing and any attempted removal requires a further surgical exploration of the site.

Many of the problems associated with oestrogen delivery for hormone replacement therapy and other long-term oestrogen-requiring conditions can be overcome by intravaginal administration of oestrogen. It is well-known that steroids in general, including oestrogens, are efficiently and rapidly absorbed through vaginal mucosal epithelium [6,7]. The vaginal route avoids undesirable first-pass hepatic metabolism. Delivery of oestrogen by the vaginal route is analogous to secretion of oestrogen into the systemic circulation by the ovary. Oestrogens may be administered intravaginally by the use of creams, solutions or vaginal tablets [2]. However, to achieve controlled-release of the oestrogenic agent, sustained over at least one month in order to enhance both patient compliance and convenience, an intravaginal device, optionally in the shape of a ring, is the most suitable drug delivery device. The intravaginal ring can be self-inserted high into the vagina where it is held in place.

U.S. Pat. No. 3,545,439 discloses an intravaginal ring fabricated from a biocompatible organopolysiloxane elastomer and containing the steroidal compound medroxyprogesterone acetate for the purpose of providing contraception in the human female. There is no teaching that such a device can be used for the administration of 17β-oestradiol precursors at a substantially constant (or zero order pattern) rate for a period of at least three weeks, for the treatment of long-term oestrogen-requiring conditions in general or, more specifically, for hormone replacement therapy.

An article by Jackanicz [8] teaches that three basic designs of intravaginal ring are possible, though additional design variations do exist:

(a) The homogeneous ring, in which the steroid is homogeneously distributed in a hydrophobic elastomeric system, typically a grade of Silastic (Trade Mark), which is commercially available from Dow Corning. In this design, a high drug loading is possible and, consequently, comparatively large daily release rates are achievable over prolonged periods. However, this design is associated with an initial high release of drug, producing a non-physiological level of the circulating steroid in the plasma, followed by a decline in the drug release rate as the outer portions of the ring are depleted of drug. Consequently, this design of ring cannot achieve the desired pattern of a controlled, substantially constant drug release rate, which will be recognised by those skilled in the art as zero order pattern release, over a sustained period of at least three weeks, preferably several months.

(b) The shell design, in which the steroid is contained in a narrow band or hollow annulus between a non-medicated central hydrophobic elastomeric core or central member and a narrow, outer non-medicated hydrophobic elastomeric sheath. The outer sheath acts as a metering, or rate-controlling, membrane. With this design, burst effects are reduced compared to the homogeneous ring. However, this design has the disadvantage that the drug reservoir is physically limited in size and the relative diameters of core, steroid band and rate-controlling sheath are such that, where comparatively high daily drug release rates are required, as in hormone replacement therapy, this design cannot achieve the desired pattern of a controlled, substantially constant comparatively high daily drug release rate for the desired period of at least three weeks, preferably several months. The shell design is, therefore, most suitable for contraception.

(c) The core design, in which the steroid is homogeneously mixed with a hydrophobic elastomeric polymer to form a homogeneous core, the core being surrounded by a rate-controlling, non-medicated hydrophobic elastomeric sheath. In this design high drug loadings are possible and the relative diameters of core and rate-controlling sheath are such that a higher drug release rate can be achieved compared to the shell design. Burst release of drug is reduced, but not necessarily eliminated, as compared to the homogeneous ring design. Substantially zero order release can be achieved due to the presence of a rate-controlling sheath and such release can be sustained for several months due to the higher drug loading possible with this design.

Intravaginal elastomeric rings designed to deliver 17β-oestradiol for use in hormone replacement therapy are known.

For example, a report by Englund and co-workers [9] discloses an intravaginal elastomeric ring of shell design releasing in vitro 17β-oestradiol at a rate of 200 μg per day, which corresponds to plasma 17β-oestradiol levels in human female patients of from 50 to 200 pg per ml. In this report, it is further disclosed that all of the human female subjects participating in the study had non-physiologically high 17β-oestradiol plasma levels in the first 24 hours of the study period and that there was a gradual decline in the plasma oestradiol levels over the study period of 21 days. There is no teaching in this study that substantially constant plasma levels of 17β-oestradiol can be maintained even within the comparatively short-term study period of 21 days, nor is there any teaching to suggest that the device could be used for the delivery of a suitable 17β-oestradiol precursor compound. This study, however, does state that a 17β-oestradiol release rate of 200 μg per day is too high for hormone replacement therapy in post-menopausal women as the resulting plasma levels of 17β-oestradiol are non-physiological, that is, they exceed the oestrogen levels seen in the follicular phase of fertile women. The authors conclude, in agreement with the teaching of Lievertz [1], that a device with a release rate of 50–100 μg per day of 17β-oestradiol would provide an appropriate dosage for hormone replacement therapy.

A study by Roy and Mishell [10] discloses an elastomeric intravaginal ring comprising a polymer matrix containing a combination of levonorgestrel and 17β-oestradiol in dimethylpolysiloxane. This study teaches that 17β-oestradiol has a lower solubility in, and diffusion from, the dimethylpolysiloxane elastomer than levonorgestrel. The ring design in this example was of the shell type, which had an outer diameter of 58 mm and a thickness of 9.5 mm, and released 290 μg per day of levonorgestrel and 180 μg per day of 17β-oestradiol, respectively. The rings were studied over six or seven consecutive 21-day cycles. In each case, 17β-oestradiol absorption produced an initial peak for the first few days of each cycle, after which plasma levels declined rapidly. The initial 17β-oestradiol serum peak was due to burst release from the outer sheath, rather than from the polymer matrix, the burst effect then building up again during each week of storage between cycles.

Thus, the ring design disclosed in this study is unsuitable for sustained delivery of 17β-oestradiol for oestrogen-requiring conditions, including hormone replacement therapy.

A study by Stumpf et al [11] on hypo-oestrogenic women discloses an intravaginal ring of shell design intended specifically for use in hormone replacement therapy. The ring was 9.5 mm in cross-section and 54 mm in diameter. The steroid band or hollow annulus contained either 100, 200 or 400 mg of 17β-oestradiol. One hour after insertion, mean serum 17β-oestradiol was raised to 300 pg/ml, characteristic of a burst release of steroid, but approached the baseline level of 24 pg/ml within 24 hours. Over 1 month, the mean 17β-oestradiol level increased minimally to about 50 pg/ml, falling back to the baseline at 2 and 3 months. The authors concluded that this design fails to provide effective therapeutic delivery of 17β-oestradiol over a sufficiently long period as desired for hormone replacement therapy.

Stumpf et al [11] also discloses an alternative intravaginal ring of homogeneous design, comprising a polymer matrix containing 400 mg of 17β-oestradiol in polydimethylsiloxane. This ring had a surface area of 22 cm² and a cross-sectional area of 48 mm². With this ring design, the initial serum 17β-oestradiol level was raised to about 700 pg/ml within one hour, with the level maintained above 300 pg/ml for at least the first week of administration. Despite the authors' conclusion that this ring design maintains physiological oestradiol levels, it will be recognised by those skilled in the art that such levels of 17β-oestradiol are non-physiological and, therefore, unacceptable for use in the human female requiring hormone replacement therapy.

European Patent Publication No. 0 253 109 discloses an intravaginal ring of core design capable of delivering 17β-oestradiol at rates per 24 hours varying from 0.5 to 25 μg per day, preferably from 4 to 8 μg per 24 hours, as selected. According to the teaching therein, symptoms in the human female arising from a hypo-oestrogenic condition can be alleviated by 17β-oestradiol delivered at these rates. These rates of 17β-oestradiol delivery are substantially lower than those generally recognised as being required to alleviate all of the possible symptoms associated with a hypo-oestrogenic condition—a daily delivery rate, as determined in vitro, of between 50 and 100 μg of 17β-oestradiol is generally accepted by those skilled in the art as necessary for effective hormone replacement therapy [1][9][11][12]. The symptoms referred to in EP-A-0 253 109 relate exclusively to symptoms associated with the lower urinogenital tract. There is no teaching that such a low daily delivery rate of 17β-oestradiol can relieve neuroendocrine and other miscellaneous symptoms associated with hypo-oestrogenism in the human female.

Smith et al [13] teaches that daily delivery of 17β-oestradiol at a rate of between 5 and 10 μg per day, as determined in vitro, is effective at alleviating those symptoms associated with hypo-oestrogenism that relate specifically to atrophy of vaginal and urethral epithelium. There is no teaching that other symptoms associated with hypo-oestrogenism are relieved by such low daily doses of 17β-oestradiol.

A number of difficulties arise in incorporating 17β-oestradiol into intravaginal drug delivery devices. Specifically, the drug is too polar in its chemical character to be practically delivered in sufficient daily quantities to alleviate all of the clinical symptoms typically associated with hypo-oestrogenism in the human female and, most particularly, in postmenopausal females requiring hormone replacement therapy with oestrogen. These difficulties mean that a daily drug release in excess of 50 μg of 17β-oestradiol, as determined in vitro, an amount clinically acknowledged as necessary for effective hormone replacement therapy, cannot be practically achieved since:

A narrow sheath surrounding a large diameter polymer matrix is difficult to mass produce reliably to acceptable limits by methods presently known in the art.

A high drug concentration is required in the polymer matrix of the device, which consequently must be of large diameter. Thus, such devices are uneconomic to produce.

The high drug residue left after use raises environmental concerns.

It is not possible to include an additional active ingredient in known intravaginal drug delivery devices, typically a progestogen.

According to a first aspect of the invention there is provided an intravaginal shell or core drug delivery device suitable for administration to a female mammal, the device comprising a 17β-oestradiol precursor as defined hereinbelow in a polymer matrix and having a sheath surrounding the polymer matrix, said device being adapted to release the 17β-oestradiol precursor in a substantially zero order pattern for at least three weeks, preferably for at least three months and to release up to 1 mg/day 17β-oestradiol.

The 17β-oestradiol precursor must:

be a 17β-oestradiol moiety in which the, or each, hydroxyl group of the 17β-oestradiol moiety is blocked by a blocking group; the, or each, blocking group being so linked to the 17β-oestradiol moiety as to be readily removed from the 17β-oestradiol moiety in vivo and the, or each, blocking group being so chosen as to yield a substance which is non-toxic to the female mammal, when removed from the 17β-oestradiol moiety in vivo.

have sufficient lipophilicity as defined hereinbelow.

have sufficient hydrophilicity as defined hereinbelow.

Specifically, the 17β-oestradiol precursors must have sufficient lipophilicity as determined directly by measurement of their solubilities in liquid silicone (Dow Corning Grade 360 Medical Fluid) at 37° C. such that their solubilities must be not less than 0.1 mg per 100 ml or, alternatively, as determined indirectly by measurement of standard k (to be defined hereinafter) such that standard k must be not less than 0.1 μg/day/mm. Such lipophilicity is required to ensure adequate diffusion of the precursor through the device.

Specifically, the 17β-oestradiol precursors must have sufficient hydrophilicity such that their solubilities in distilled water at 20° C. are not less than 1 μg per 100 ml. Such hydrophilicity is required to ensure that an adequate concentration of the precursor is achieved in the aqueous diffusion layer between the device and the vaginal epithelium.

Precursor release from a cylindrical device of core design, which comprises a polymer matrix in the form of a core incorporating 17β-oestradiol precursor and a sheath surrounding the core, can be described by Crank's equation:

$$R = \frac{2 \cdot \pi \cdot C_s \cdot l \cdot D}{\ln(b/a)}$$

in which

R=precursor release rate (μg/day)

$C_S$=saturation solubility of precursor in polymer matrix (μg/ml)

D=diffusion coefficient of precursor in polymer matrix (cm²/day)

π=partition coefficient of precursor between polymer matrix and the dissolution medium l=core length (mm)

b=sheath cross-sectional diameter (mm)

a=core cross-sectional diameter (mm)

Crank's equation relates the precursor release rate (R), in sink conditions, to the solubility ($C_{2\,S}$) and diffusibility (D) of the precursor in the polymer matrix, its partition characteristics (π) between the polymer matrix and the dissolution medium; and the ring dimensions (l, b, a). For any given precursor in any given polymer matrix, $C_S$, D and π will be constant and can be grouped together to form the composite constant, k:

$$k = 2C_S . D . \pi$$

The k value can be empirically derived using Crank's equation in the following manner:

$$k = \frac{R \cdot \ln(b/a)}{l}$$

The k value is dependent on core length for certain of the 17β-oestradiol precursors (see Example 6 hereinafter). Accordingly, the k value at a core length of 35 mm has been denoted "standard k" value hereinafter.

The use of 17β-oestradiol precursors with enhanced lipophilicity, relative to 17β-oestradiol itself, is one parameter involved in overcoming the difficulties which arise in incorporating 17β-oestradiol itself into intravaginal drug delivery devices. However, only 17β-oestradiol precursors possessing the above-recited additional physicochemical property of sufficient hydrophilicity and clinical characteristics of ready in vivo conversion to 17β-oestradiol without yielding toxic substances as a result of that conversion, are suitable for use in intravaginal devices for the delivery of therapeutic quantities of oestrogen to the human female for long-term oestrogen-requiring conditions, including hormone replacement therapy. In addition, such 17β-oestradiol precursors are also suitable for fertility control. Thus, for example, 17β-oestradiol-17-valerate, a highly hydrophobic precursor, will not give detectable blood levels of 17β-oestradiol in the human female when delivered intravaginally from an intravaginal drug delivery device, since its hydrophilicity or aqueous solubility is too low. The invention therefore defines the characteristics of 17β-oestradiol precursors, and identifies those suitable precursors, such that an intravaginal drug delivery device containing said precursors will deliver therapeutic quantities of 17β-oestradiol to the female mammal without any of the disadvantages previously associated with such systems.

Whilst it will be apparent that said intravaginal drug delivery device can have any shape and be of any dimensions compatible both with intravaginal administration to the female mammal, including the human female and with the requirements imposed by drug delivery kinetics, a particularly preferred device according to the present invention is an intravaginal ring.

Said ring includes the outer, rate-controlling sheath surrounding the polymer matrix in the form of a core, which sheath may be fabricated from the same polymer as that of the polymer matrix or from any other suitable, compatible polymer known in the art. Alternatively, said ring includes the sheath surrounding the polymer matrix in the form of a hollow annulus and the device is provided with a central member within the annulus, which sheath and central member may each be fabricated from the same polymer as that of the polymer matrix or from any other suitable, compatible polymer known in the art.

More preferably, daily release rates of the 17β-oestradiol precursor equivalent to up to 1 mg per day of 17β-oestradiol itself can be sustained for up to at least 12 months in a substantially zero order pattern.

Preferably, said intravaginal drug delivery device additionally includes a progestogen in the polymer matrix, the progestogen being selected from the group comprising norethisterone-17-acetate and levonorgestrel. Said 17β-oestradiol precursor can be delivered in a substantially zero order pattern for durations of at least three weeks and, preferably, up to 12 months at rates of delivery equivalent to up to 1 mg per day of 17β-oestradiol itself and said progestogen can be delivered for a similar duration at rates of delivery of up to 1 mg per day.

According to a second aspect of the invention there is provided use of a suitable 17β-oestradiol precursor as defined hereinbefore for the manufacture of an intravaginal shell or core drug delivery device for daily release of up to 1 mg 17β-oestradiol in a substantially zero order pattern for at least three weeks and, preferably, for up to 12 months for treating hypo-oestrogenic symptoms. The diameter of a rate-controlling sheath is such that it can be manufactured within acceptable tolerances by methods presently known in the art.

According to a third aspect of the invention there is provided a process for the preparation of an intravaginal shell or core drug delivery device suitable for administration to a female mammal. Said process comprises the steps of combining a suitable 17β-oestradiol precursor as defined hereinabove, a polymer, a suitable cross-linking agent and a curing catalyst to form a mix; curing the mix to form the polymer matrix; and providing a sheath surrounding the polymer matrix.

Alternatively, the polymer matrix forms a hollow annulus and the process comprises the steps of forming a central member; combining the 17β-oestradiol precursor with the polymer, the suitable cross-linking agent and the curing catalyst to form the mix and curing the mix to form the polymer matrix in the form of the hollow annulus surrounding the central member; and providing the sheath surroundiong the polymer matrix. The relative amounts of the respective polymer matrix and sheath components are chosen, and the geometry of the ring components selected, in order to provide a daily release of 17β-oestradiol precursor equivalent to between 50 and 250, and most preferably between 50 and 100, μg per day of 17β-oesstradiol.

According to a fourth aspect of the invention there is provided use of a suitable 17β-oestradiol precursor as defined hereinabove in an intravaginal shell or core drug delivery device for release of up to 1 mg/day 17β-oestradiol in a substantially zero order pattern for at least three weeks and, preferably, for up to 12 months.

According to the present invention, a particularly preferred group of 17β-oestradiol precursors are those possessing one or more acyl groups esterically linked as blocking groups to the hydroxyl groups of the 17β-oestradiol moiety. Preferably, the, or each, blocking group is an aliphatic short-chain acyl group with the proviso that, when the acyl group is acetyl, each hydroxyl group cannot be blocked with acetyl. More preferably, the acyl group is the acyl moiety of a saturated or unsaturated monocarboxylic or dicarboxylic acid. The one or more acyl groups may block the 3-position and/or the 17-position of the 17β-oestradiol moiety. It will be known to those skilled in the art that therapeutically active esters are rapidly hydrolysed in human plasma by non-specific esterases to the corresponding parent acid and alcohol. In the case of 17β-oestradiol precursors, it will be apparent to those skilled in the art that hydrolysis of said precursors in human plasma will yield 17β-oestradiol itself, together with one or more acidic components, the number of such acidic components depending on the number of acyl groups present per molecule of said precursor. Said acyl groups include saturated aliphatic short-chain (C1-5) straight or branched mono- and dicarboxylic acids such as formyl, acetyl, propionyl, butyryl, isobutyryl, oxalyl, malonyl, glutaryl and succinyl; unsaturated aliphatic short-chain (C2-5) straight or branched mono- and dicarboxylic acids such as acryloyl, propioloyl, methacryloyl, crotonoyl, isocrotonoyl, maleoyly fumaroyl, citraconoyl and mesaconoyl; carbocyclic carboxylic acids or other such groups known to those skilled in the art. Such acyl groups are disclosed by way of example only and it will be understood that the scope of the invention is not limited in any way by such disclosure.

The preferred 17β-oestradiol precursors must have sufficient lipophilic character such that their solubilities in liquid silicone (Dow Corning Grade 360 Medical Fluid) at 37° C. are not less than 0.1 mg per 100 ml. Alternatively, the preferred 17μ-oestradiol ester precursors must have sufficient lipophilic character such that their standard k values (as defined hereinabove) are not less than 0.1 μg/day/mm.

Further, said precursors must have a hydrophilic character such that their solubilities in distilled water at 20° C. are not less than 1 μg per 100 ml. 17β-oestradiol-3-benzoate and 17β-oestradiol-17-valerate are examples of 17β-oestradiol precursors not possessing the requisite aqueous solubility.

Although not essential for the purposes of the invention, said precursors should, preferably, be micronised.

According to the present invention, a preferred acyl group is acetyl or propionyl and particularly preferred 17β-oestradiol precursors are 17β-oestradiol-17-acetate, 17β-oestradiol-3-acetate, 17β-oestradiol-17-propionate and 17β-oestradiol-3-propionate.

According to the present invention, the acyl group preferably blocks the 3-position, so that particularly preferred 17β-oestradiol precursors are 17β-oestradiol-3-acetate and 17β-oestradiol-3-propionate. 17β-oestradiol-3-acetate is most particularly preferred.

Suitable progestogens for use in the intravaginal drug delivery devices of the present invention include, but are not limited to, levonorgestrel and norethisterone-17-acetate. Further suitable progestogens would be expected to include chlormadinone, desorgestrel, gestodene, medroxyprogesterone, megestrol, norgestimate and progesterone.

The intravaginal ring may be constructed from one or more biocompatible polymers, for example, elastomers, compatible with said 17β-oestradiol precursors, such as organopolysiloxanes or polyurethanes. Where the elastomer is chosen from the room-temperature vulcanising type of hydroxyl-terminated organopolysiloxanes, suitable cross-linking agents and curing catalysts known in the art may be required. Dimethylpolysiloxane compositions may also be used as the elastomeric component of the intravaginal drug delivery device of the invention.

The geometry of the intravaginal drug delivery device of the invention may be chosen such that the daily release of the 17β-oestradiol precursor can be varied up to 1 mg per day, expressed as 17β-oestradiol itself, and preferably from between 50 to 100 μg per day, again expressed as 17β-oestradiol itself. Said ring geometries can also be varied to permit the simultaneous delivery, at therapeutically desirable rates, from an individual intravaginal drug delivery device, of a suitable 17β-oestradiol precursor and a progestogenic substance. The term "geometry" encompasses the overall diameter of the ring; the cross-sectional diameter of the ring; the ratio of the core diameter to the diameter of the whole device in cross-section; and the length of the core.

The percentage loading of 17β-oestradiol precursor contained in the core can vary from 1% (w/w) to in excess of 50% (w/w) and is only limited by the physical characteristics of the final mix. It will be apparent to those skilled in the art that the only importance of said drug loading in a device of core or shell design with an outer, rate-controlling sheath is to ensure that there is sufficient drug present at all times to allow a substantially zero order pattern of drug release to be maintained throughout the required period of sustained drug release. Thus, to ensure maintenance of the substantially zero order drug release pattern throughout the lifetime of the device, the necessary drug loading will be sufficiently in excess of the total drug required to be delivered over the defined sustained-release period.

Several embodiments of the invention will now be demonstrated by reference to the following General Method of Manufacture of an intravaginal drug delivery device in the form of a ring for the delivery of a suitable 17β-oestradiol precursor as defined hereinabove, either alone or in combination with a progestogenic substance. This General Method of Manufacture is exemplified by reference to Examples 1 to 10. It should be understood that these examples are disclosed solely by way of further illustrating the invention and should not be taken in any way to limit the scope of said invention. Thus, for instance, it will be obvious to those skilled in the art that the technique of injection moulding referred to in the General Method of Manufacture may be replaced in whole or in part by other manufacturing techniques, for example, extrusion, that will produce a similar end product.

General Method of Manufacture: Core Design

An elastomer mix is prepared by blending 97 parts by weight of a hydrophobic elastomeric polymer containing about 25% (w/w) diatomaceous earth as the filler with 2.5 parts by weight of a cross-linking agent, n-propylorthosilicate. A suitable hydrophobic elastomeric polymer is stannous octoate-cured polydimethylsiloxane polymer, two suitable examples of which are those known as Dow Corning QCF7 3099 and Nusil Med 7.6382.

The elastomer mix thus formed is further blended in the ratio of 85 parts by weight of the elastomer mix, 5 parts by weight of barium sulphate and 10 parts by weight of a 17β-oestradiol precursor, preferably a 17β-oestradiol ester, more preferably, 17β-oestradiol-3-acetate, 17β-oestradiol-17-acetate, 17β-oestradiol-3-propionate or 17β-oestradiol-17-propionate. Thereby, an active mix is formed.

The core of the intravaginal drug delivery device of the invention is produced by mixing 200 parts by weight of the active mix with 1 part by weight of an activating catalyst, for example, stannous octoate. The resultant core mix is injected into a core mould and cured at 80° C. for 2 minutes. The mould is then opened, following which the core is removed and trimmed.

An intravaginal drug delivery device in the form of a half ring is produced by mixing 200 parts by weight of elastomer mix with 1 part by weight of an activating catalyst, for example, stannous octoate. The resultant half ring mix is injected into a half ring mould containing a core previously prepared as described in the immediately preceding paragraph and cured at 80° C. for 2 minutes. The mould is then opened, following which the half ring is removed and trimmed.

An intravaginal drug delivery device in the form of a complete ring is produced by mixing 200 parts by weight of elastomer mix with 1 part by weight of an activating catalyst, for example, stannous octoate. The resultant full ring mix is injected into a full ring mould containing a half ring previously prepared as described in the immediately preceding paragraph and cured at 80° C. for 2 minutes. The mould is then opened, following which the full ring is removed and trimmed.

The geometric characteristics of the ring can be varied as required by the use of appropriately sized moulds, as exemplified by the following examples, or by the use of appropriately sized extrusion nozzles, as will be obvious to those skilled in the art.

EXAMPLE 1

An intravaginal drug delivery device in the form of a ring having a nominal in vitro daily release rate of 10 μg per day of 17β-oestradiol-17-acetate was prepared with a ring geometry as described in Table 1, by following the General Method of Manufacture set out hereinabove.

EXAMPLE 2

An intravaginal drug delivery device in the form of a ring having a nominal in vitro daily release rate of 50 µg per day of 17β-oestradiol-17-acetate was prepared with a ring geometry as described in Table 1, by following the General Method of Manufacture set out hereinabove.

EXAMPLE 3

An intravaginal drug delivery device in the form of a ring having a nominal in vitro daily release rate of 50 µg per day of 17β-oestradiol-3-acetate was prepared with a ring geometry as described in Table 1, by following the General Method of Manufacture set out hereinabove.

EXAMPLE 4

An intravaginal drug delivery device in the form of a ring having a nominal in vitro daily release rate of 100 µg per day of 17β-oestradiol-3-acetate was prepared with a ring geometry as described in Table 1, by following the General Method of Manufacture set out hereinabove.

EXAMPLE 5

An intravaginal drug delivery device in the form of a ring having a nominal daily in vitro release rate of, simultaneously, 50 µg per day of 17β-oestradiol-3-acetate and 20 µg per day of the progestogenic substance, levonorgestrel, was prepared with a ring geometry as described in Table 1, by following the General Method of Manufacture set out hereinabove.

The nominal in vitro release rates set out in Table 1 for the rings of Examples 1–5 were determined under sink conditions of 1% (w/v) benzalkonium chloride. These release rates were determined in the following manner.

Each ring (n=4) was suspended in the dissolution medium in an individual flask which is then capped, placed in a suitable oven at 37° C. and shaken. The dissolution medium was changed every 24 hours (±30 minutes). An aliquot of the used dissolution medium was analysed by high performance liquid chromatography (HPLC) using reverse phase packing and UV detection (at 235 nm for 17β-oestradiol-3-acetate and for 17β-oestradiol-3-propionate; at 281 nm for 17β-oestradiol-17-acetate, for 17β-oestradiol-17-propionate and for 17β-oestradiol), with reference to the appropriate standard solutions. Due to hydrolysis to 17β-oestradiol during storage, 17β-oestradiol-3-acetate levels were determined by analysis for both 17β-oestradiol and 17β-oestradiol-3-acetate. An improved analytical method was subsequently developed for 17β-oestradiol-3-acetate—this involves hydrolysing an aliquot of used dissolution medium with 0.5N NaOH to yield 17β-oestradiol with subsequent buffering prior to injection into the HPLC system for detection at 281 nm of the hydrolysis product, 17β-oestradiol, with reference to the appropriate standard solutions.

The original analytical method has a precision of less than 2% RSD (relative standard deviation) for 17β-oestradiol and for the 17β-oestradiol precursors, with the exception of 17β-oestradiol-3-acetate for which the original and improved analytical methods had precisions of less than 4% RSD and less than 2% RSD, respectively. The sensitivity of the original and improved analytical methods is 5 µg/100 ml.

Re-analysis of the daily in vitro release rate data for 17β-oestradiol-3-acetate given in Table 1 from the original method, yields altered daily release rates which, in turn, result in corrected precursor-containing core dimensions of 2×10 mm, 2×20 mm and 2×10 mm respectively, for the rings of Examples 3–5, in order to nominally release 50 µg, 100 µg and 50 µg/day, respectively, of the active ingredient, 17β-oestradiol-3-acetate.

EXAMPLE 6

Mean Daily In Vitro Release Rates over 90 Days (Maximum)

The in vitro dissolution characteristics of the intravaginal rings of the invention, which contain various 17β-oestradiol precursors, and of an intravaginal ring containing 17β-oestradiol itself are illustrated by reference to Table 2. Four identical rings were prepared for each compound according to the General Method of Manufacture, the elastomer mix having a stannous octoate-cured polydimethylsiloxane polymer as the hydrophobic elastomeric polymer. In all cases the ring geometries comprise a ring of dimensions 9 mm (cross-sectional diameter)×54 mm (outer diameter) and containing a full length core (141 mm) of cross-sectional diameter 2 mm. The rings were tested in vitro at a constant temperature of 37° C. for their release characteristics in a sufficient volume of each of the following media: 0.9% (w/v) saline,

TABLE 1

Drug-loaded core dimensions for intravaginal rings, 9 × 54 mm, having a nominal in vitro daily release, in sink conditions, of a 17β-oestradiol precursor, either alone or in combination with a progestogen.

| Active ingredient | Example | Nominal daily release (µg) (in vitro) | Core dimensions (mm) as cross-sectional diameter × length |
|---|---|---|---|
| 17β-oestradiol-17-acetate | 1 | 10 | 2 × 15 |
| 17β-oestradiol-17-acetate | 2 | 50 | 2 × 75 |
| 17β-oestradiol-3-acetate | 3 | 50 | 2 × 8 |
| 17β-oestradiol-3-acetate | 4 | 100 | 2 × 16 |
| 17β-oestradiol-3-acetate (E3A) in combination with levonorgestrel (LN) | 5 | 50 E3A and 20 LN | 2 × 8(E3A) 3 × 105(LN) |

0.133% (w/v) aqueous benzalkonium chloride and 1.0% (w/v) aqueous benzalkonium chloride. The saline medium was chosen because the ability of a particular 17β-oestradiol precursor to achieve substantial release from an intravaginal ring into saline may be regarded as a significant indicator of its likely in vivo absorption characteristics. The saline and benzalkonium chloride-containing media were chosen to ensure 'sink conditions' in at least one medium for each intravaginal ring. It will be recognised by those skilled in the art that the term 'sink conditions' refers to that set of experimental conditions in vitro which effectively simulates the active haemoperfusion that occurs in vivo, and which results in a maximum drug concentration gradient and maximum drug diffusion

TABLE 2

Mean daily release rates of 17β-oestradiol and 17β-oestradiol precursors from intravaginal rings into various media. Rings were 9 × 54 mm containing a drug-loaded core of full length (141 mm) having a cross-sectional diameter of 2 mm.

| Active ingredient | Mean Daily Release μg per day (N = 4) Release Medium | | |
|---|---|---|---|
| | 0.9% (w/v) saline | 0.133% (w/v) BKC* | 1.0% (w/v) BKC* |
| 17β-oestradiol | 8 | — | — |
| 17β-oestradiol-17-valerate | ** | 365 | 550 |
| 17β-oestradiol-17-propionate | 26 | 112 | 218 |
| 17β-oestradiol-17-acetate | 24 | S6 | 96 |
| 17β-oeastradiol-3- | <5 | 42 | 66 |
| 17β-oestradiol-3-acetate | 350 | 700 | 850 |
| 17β-oestradiol-3-propionate | — | — | 1200 |

*BKC = benzalkonium chloride in aqueous solution
**Not detected
— Not determined rate, at any given time, across the aqueous boundary layer. Thus, an in vitro dissolution experiment can be designed such that the solution solubility of the released drug in the dissolution medium is much greater than its bulk concentration in this medium at any given time, for example, by micellar drug solubilisation due to incorporation of a surfactant such as benzalkonium chloride (BKC), at a concentration above its critical micelle concentration.

Thus, each ring was suspended by a thread in an individual closed flask containing the dissolution medium, maintained at a constant temperature of 37° C. The contents of the flask were gently agitated in order to prevent the occurrence of a hydrostatic layer on the surface of the ring. After 24 hours, the ring was removed and suspended in a flask of fresh dissolution medium of identical volume by a method identical to that previously described. This process was repeated at each successive 24 hour interval until a total maximum time of 90 days had elapsed. At the end of each 24 hour period, a sample of the dissolution medium was immediately analysed, as desired, for its precurser content by a suitable analytical method, typically by high performance liquid chromatography (see Example 5).

The data in Table 2 refer to mean daily in vitro release rates of 17β-oestradiol and various 17β-oestradiol precursors as determined by the method described, in each of the three specified release media, over a continuous period of up to 90 days. Sink conditions were evident for the 17β-oestradiol precursors in 1.0% BKC. The low release rates into saline of the more lipophilic 17β-oestradiol precursors, the valerate and benzoate esters, were due to their intrinsically low aqueous solubilities. The best release rates under sink conditions, in combination with substantial aqueous solubilities as indicated by the release rates into saline, were observed for the acetate and propionate esters. Thus, in particular, 17β-oestradiol-3-acetate exhibited substantial release, in both BKC and in saline, from intravaginal rings of ring geometry as described in Table 2.

Figure 1:
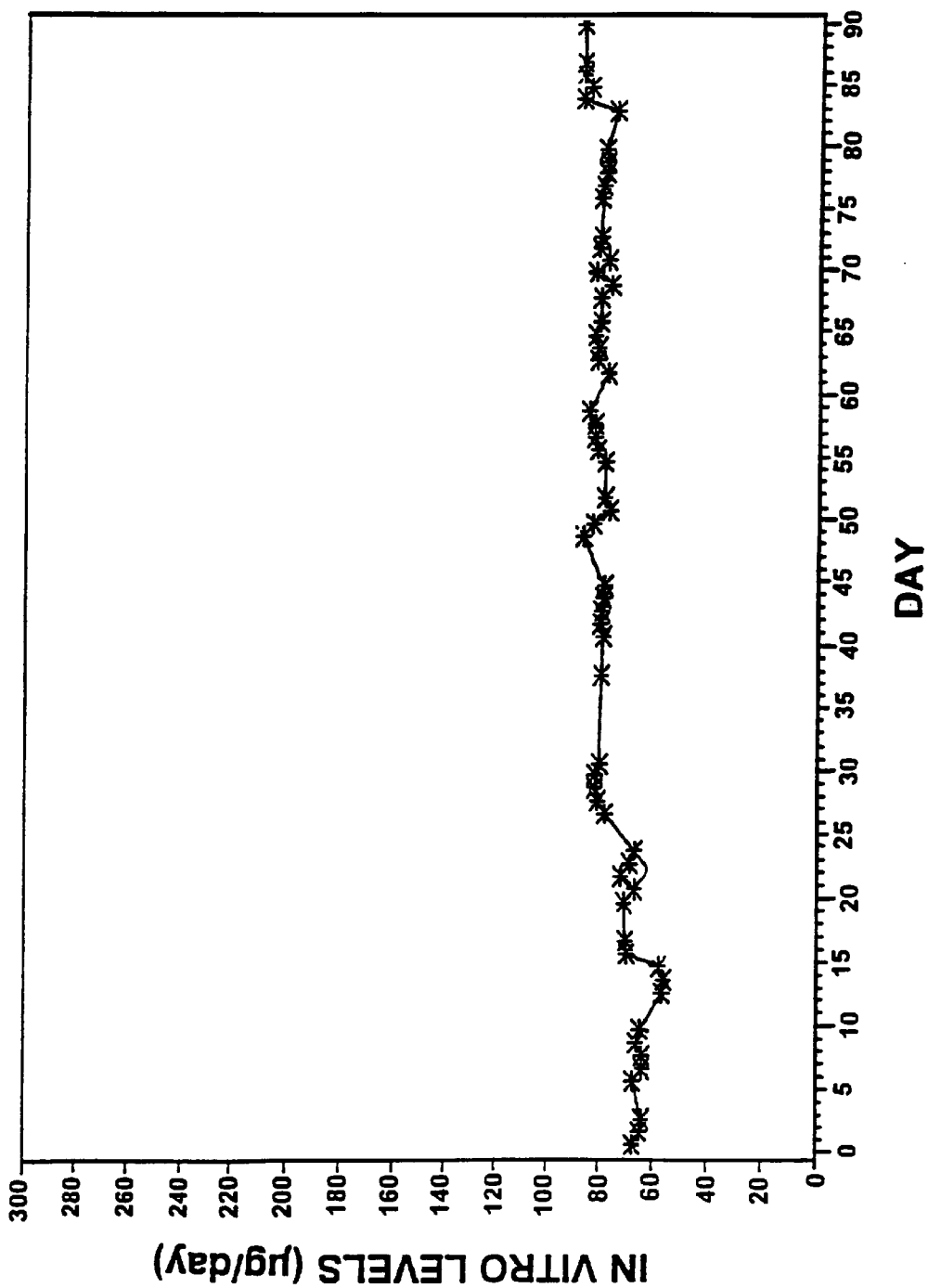
FIG. 1 of the accompanying drawings shows the in vitro daily release of 17β-oestradiol-17-acetate (as 17β-oestradiol) from a 9×54 mm intravaginal ring (core length of 141 mm and core cross-sectional diameter of 2 mm) over 90 days into a 1.0% (w/v) aqueous solution of benzalkonium chloride. The ring was prepared by following the General Method of Manufacture set out hereinabove.
Figure 2:
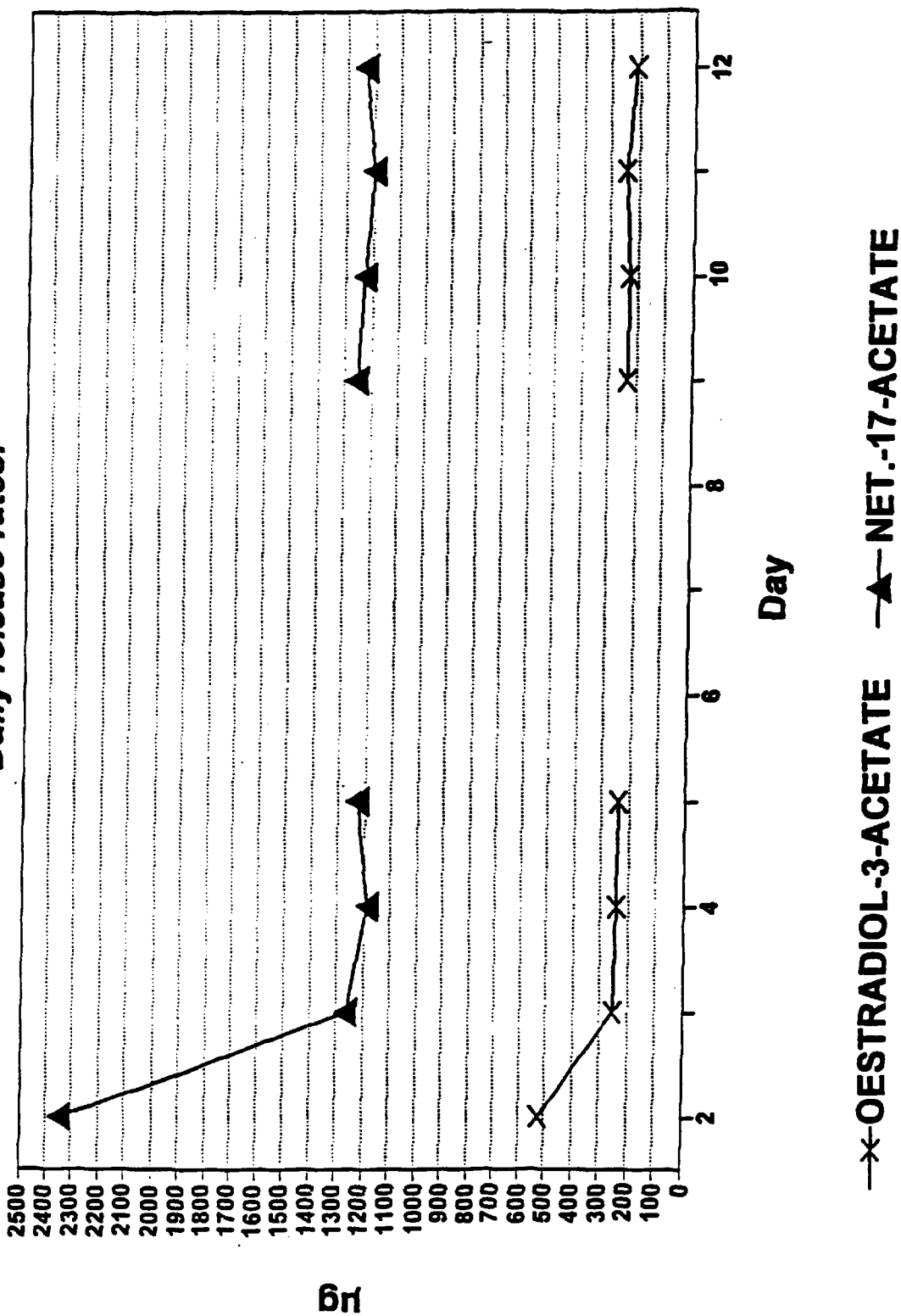
FIG. 2 of the accompanying drawings shows the in vitro daily release from a 7.6×56 mm ring of 17β-oestradiol-3-acetate (as 17β-oestradiol (core length 35 mm; core cross-sectional diameter 2 mm)) and norethisterone-17-acetate (core length 90 mm; core cross-sectional diameter 2 mm) over 12 days into a 1.0% (w/v) aqueous solution (250 ml) of benzalkonium chloride. The ring was prepared by following the General Method of Manufacture set out hereinabove.

The data presented in the figures confirm the efficacy of intravaginal drug delivery devices according to the present invention in releasing 17β oestradiol in vitro in a substantially zero order pattern over the up to 90 day period of study.

TABLE 3

Mean daily release rates of 17β-oestradiol precursors into 250 ml of 1% (w/v) benzalkonium chloride. Rings were 9 × 54 mm containing a drug-loaded core of varying length having a cross-sectional diameter of 2 mm.

| Active ingredient | Core length (mm) | Mean Daily Release (μg/day) (n = 5) (as precursor)* | k |
|---|---|---|---|
| 17β-oestradiol-3-acetate | 6 | 49.25 | 12.347 |
| | 12 | 91.88 | 11.517 |
| | 25 | 177.15 | 10.658 |
| | 35 | 236.66 | 10.017 |
| 17β-oestradiol-3-propionate | 35 | 300.00 | 12.89 |
| | 70 | 600.00 | 12.89 |
| | 140 | 1200.00 | 12.89 |
| 17β-oestradiol-17-acetate | 35 | 19.50 | 0.8380 |
| | 70 | 40.94 | 0.8797 |
| | 140 | 87.45 | 0.9395 |
| 17β-oestradiol-17-propionate | 17 | 24.08 | 2.130 |
| | 35 | 42.86 | 1.842 |
| | 70 | 83.54 | 1.795 |
| | 140 | 155.20 | 1.667 |

*The release rate data for 17β-oestradiol-3-acetate are based on the amount of anhydrous 17β-oestradiol detected by the improved analytical method. These data have been converted to 17β-oestradiol as 17β-oestradiol-3-acetate by multiplication by the correction factor 1.154.

Intravaginal drug delivery devices in the form of rings were prepared, each with a ring geometry as described in Table 3, by following the General Method of Manufacture set out hereinabove. Table 3 also shows in vitro release rates into 1% (w/v) benzalkonium chloride for these rings and the apparent k values observed when the core length is varied.

The dissolution medium was changed daily, following the protocol set out hereinabove. Mean daily release rates from the second week of dissolution experiments were used to determine the apparent k values presented in Table 3.

It will be observed that the apparent k value varies with core length for 17β-oestradiol-3-acetate, 17β-oestradiol-17-acetate and 17β-oestradiol-17-propionate. It was, therefore, decided to determine k values at a core length of 35 mm and such k values are hereinafter referred to as "standard k" values.

EXAMPLE 7

Solubility Parameters for 17β-Oestradiol and Certain 17β-Oestradiol Precursors

The standard k value was determined from the mean daily release rates observed in Example 6. The dissolution medium of 1.0% (w/v) of an aqueous solution of benzalkonium chloride was used in respect of the various 17β-oestradiol precursors, so as to ensure sink conditions. The relevant data are presented in Table 4.

Aqueous solubility was determined at 20° C. in distilled water. The relevant data are presented in Table 5.

Silicone solubility was determined at 37° C. in Dow Corning (Trade Mark) 360 medical fluid. The relevant data are presented in Table 5.

EXAMPLE 8

In Vitro Plasma Hydrolysis

The stability of 17β-oestradiol-3-acetate and 17β-oestradiol-17-acetate were determined in human blood by incubation at 37° C. at concentrations of 100 pg/ml and 500 pg/ml—these concentrations were chosen to be of the same order or slightly higher than circulating 17β-oestradiol levels expected from use of an intravaginal drug delivery device according to the invention. In addition, a supranormal concentration of 10 ng/ml was also investigated.

Samples were collected at 1, 5, 10, 15, 30 and 60 minutes and at 2, 4, 6 and 24 hours after commencement of incubation. On collection of each sample, the reaction was stopped by the addition of sodium fluoride (0.05–0.1M final concentration), the plasma separated by centrifugation and analysed for 17β-oestradiol using ELISA on a Behring OPUS Plus instrument, by reference to the appropriate standard solutions.

The hydrolysis half-lives for 17β-oestradiol-3-acetate and 17β-oestradiol-17-acetate were <1 minute and 4 hours, respectively.

EXAMPLE 9

In Vivo Characteristics

The in vivo dissolution characteristics of intravaginal drug delivery devices according to the invention were assessed in the following manner.

TABLE 4

Mean daily release rates of 17β-oestradiol precursors from intravaginal rings into various media. Rings were 9 × 54 mm containing a drug-loaded core of 35 mm length having a cross-sectional diameter of 2 mm.

| Active ingredient | Mean Daily Release (μg/day) (n = 5) Release medium | | Standard k |
|---|---|---|---|
| | 0.9% (w/v) saline | 1.0% (w/v) BKC | |
| 17β-oestradiol-3-acetate | — | 236.66 | 10.017 |

TABLE 4-continued

Mean daily release rates of 17β-oestradiol precursors from intravaginal rings into various media. Rings were 9 × 54 mm containing a drug-loaded core of 35 mm length having a cross-sectional diameter of 2 mm.

| Active ingredient | Mean Daily Release (μg/day) (n = 5) Release medium | | Standard k |
|---|---|---|---|
| | 0.9% (w/v) saline | 1.0% (w/v) BKC | |
| 17β-oestradiol-3-propionate | 250–350 | 300.00 | 12.89 |
| 17β-oestradiol-17-acetate | — | 19.50 | 0.838 |
| 17β-oestradiol-17-propionate | — | 42.86 | 1.842 |

— not determined

TABLE 5

| Active Ingredient | Aqueous solubility (μg/100 ml) | Silicone solubility (mg/100 ml) | k (μg/day/mm) |
|---|---|---|---|
| 17β-Oestradiol | 190 | 1.63[1] | 0.09*** |
| 17β-Oestradiol-17-valerate | * | 15.02[1] | 5.86*** |
| 17β-Oestradiol-17-propionate | 5 | — | 1.842** |
| 17β-Oestradiol-17-acetate | 12 | 1.7 | 0.838** |
| 17β-Oestradiol-3-benzoate | * | 3.68[1] | 0.70*** |
| 17β-oestradiol-3-acetate | 380 | 18.6 | 10.017** |
| 17β-Oestradiol-3-propionate | 230 | 30.0 | 12.89** |

*not detected
— not determined
**standard k
***k using core of 141 mm length
[1]compiled from Novel Drug Delivery Systems; Yie W. Chien; Marcel Dekker, Inc.

Intravaginal rings containing the 17β-oestradiol precursors, 17β-oestradiol-3-acetate or 17β-oestradiol-17-acetate, were prepared according to the General Method of Manufacture, having a stannous octoate-cured polydimethylsiloxane polymer as the hydrophobic elastomeric polymer. The 9×54 mm rings have nominal in vitro daily release rates of 115–125 or 230–250 μg (each calculated as anhydrous 17β-oestradiol) or 100 μg (hereinafter referred to as "120 μg" or "240 μg" or "100 μg" rings, respectively), by virtue of respective core dimensions of 2×24 mm and 2×47 mm and 2×141 mm (cross-sectional diameter×length).

Several female post-menopausal subjects, who gave informed consent before participation, entered a randomised cross-over study of 18 weeks duration in which, following a run in period of 2 weeks (for baseline plasma oestradiol determinations), each subject successively received each of a 100 μg, 120 μg and 240 μg ring, with a washout period of 2 weeks between successive rings. The rings were inserted on Day 0 and removed on Day 28. Plasma 17β-oestradiol levels were regularly measured during the run in period before the start of the study, immediately preceding insertion on Day 0 and for the following four week period ending on Day 28, when the ring was removed. The observed mean plasma 17β-oestradiol levels are set out in Tables 6, 7 and 8.

TABLE 6

120 μg ring (n = 5): 17β-Oestradiol-3-Acetate

| Day | Mean Plasma 17β-Oestradiol level (pmol/l) |
|---|---|
| −14 | 46.0 |
| −10 | 49.6 |
| −5 | 43.0 |
| 0 | 48.6 |
| 2 | 431.0 |
| 4 | 394.4 |
| 7 | 364.0 |
| 9 | 359.8 |
| 11 | 350.0 |
| 14 | 371.8 |
| 18 | 321.4 |
| 21 | 338.8 |
| 28 | 284.0 |

It will be observed that the mean baseline 17β-oestradiol level was 46.8 pmol/l and that the mean 17β-oestradiol level, post-ring insertion, was 357.24 pmol/l. Thus, the 120 μg ring according to the invention delivered a mean increase in plasma 17β-oestradiol of 310.4 pmol/l over the 28 day study period.

TABLE 7

240 μg ring (n = 5): 17β-Oestradiol-3-Acetate

| Day | Mean Plasma 17β-Oestradiol level (pmol/l) |
|---|---|
| −14 | 46.0 |
| −10 | 49.6 |
| −5 | 43.0 |
| 0 | 35.8 |
| 2 | 817.4 |
| 4 | 697.2 |
| 7 | 676.6 |
| 9 | 667.8 |
| 11 | 645.0 |
| 14 | 671.2 |
| 18 | 667.2 |
| 21 | 642.8 |
| 28 | 665.2 |

It will be observed that the mean baseline 17β-oestradiol level was 43.6 pmol/l and that the mean 17β-oestradiol level, post-ring insertion, was 683.37 pmol/l. Thus, the 240 μg ring according to the invention, delivered a mean increase in plasma 17β-oestradiol of 639.7 pmol/l over the 28 day study period.

TABLE 8

100 μg ring (n = 4): 17β-Oestradiol-17-Acetate

| Day | Mean Plasma 17β-Oestradiol level (pmol/l) |
|---|---|
| −14 | 46.00 |
| −10 | 49.60 |
| −5 | 43.00 |
| 0 | 55.75 |
| 2 | 193.00 |
| 4 | 110.25 |
| 7 | 103.25 |
| 9 | 91.25 |
| 11 | 89.50 |
| 14 | 95.75 |
| 18 | 87.25 |
| 21 | 104.00 |
| 28 | 102.50 |

It will be observed that the mean baseline 17β-oestradiol level was 48.59 pmol/l and that the mean 17β-oestradiol level, post-ring insertion, was 108.53 pmol/l. Thus, the 100 μg ring according to the invention, delivered a mean increase in plasma 17β-oestradiol of 59.94 pmol/l over the 28 day study period.

It will be appreciated that the 120 μg and 240 μg rings of the present invention will be suitable for the alleviation or prevention of symptoms associated with hypo-oestrogenism, specifically hormone replacement therapy and for inducing hyper-oestrogenism, specifically to prevent ovulation. It will also be appreciated that the 100 μg ring of the present invention will be suitable for hypo-oestrogenism responding to low dose hormone replacement therapy and that a ring having a larger core diameter would, of course, release more oestradiol precursor and, therefore, deliver more 17β-oestradiol into the blood stream.

The data presented in Tables 6–8 confirm the efficacy of intravaginal drug delivery devices according to the present invention in releasing 17β-oestradiol into the blood stream in a substantially zero order pattern over the 28 day period of study.

EXAMPLE 10

In Vivo Characteristics

Intravaginal rings containing the 17β-oestradiol precursor, 17β-oestradiol-3-acetate, were prepared according to the General Method of Manufacture, having a stannous octoate-cured polydimethylsiloxane polymer as the hydrophobic elastomeric polymer. The 9×54 mm rings have a nominal in vitro daily release rate of 57.5–62.5 μg calculated as anhydrous 17β-oestradiol (hereinafter referred to as a "60 μg" ring) by virtue of dimensions of 2×12 mm (cross-sectional diameter×length).

Six female post-menopausal subjects, who gave informed consent before participation, received the 60 μg intravaginal ring. These rings were inserted on Day 0 and removed on Day 14. Plasma 17β-oestradiol levels were measured on Day 0 and regularly during the two week period and the results are set out in Table 9.

TABLE 9

60 μg ring (n = 6): 17β-Oestradiol-3-Acetate

| Day | Mean Plasma 17β-oestradiol level (pmol/l) |
|---|---|
| 0 | 31.5 |
| 2 | 229.3 |
| 4 | 146.8 |
| 7 | 131.5 |
| 9 | 139.8 |
| 11 | 114.8 |
| 14 | 134.7 |

It will be observed that the mean baseline 17β-oestradiol level was 31.5 pmol/l and that the mean 17β-oestradiol level, post-ring insertion, was 149.48 pmol/l. Thus, the 60 μg ring according to the present invention, delivered a mean increase in plasma 17β-oestradiol of 117.98 pmol/l over the 14 day study period.

It will be appreciated that the 60 μg ring of the present invention will be suitable for the alleviation or prevention of symptoms associated with hypo-oestrogenism, specifically, hormone replacement therapy.

It will also be appreciated that the 60 μg ring of the present Example and the 120 and 240 μg rings of Example 9 demonstrate a core length-dependent delivery of 17β-oestradiol into the blood stream in a substantially zero order pattern. The core length can, therefore, be adjusted to yield the desired incremental plasma 17β-oestradiol level to treat symptoms associated with hypo-oestrogenism or to induce hyper-oestrogenism.

REFERENCES CITED

1. Lievertz, R. W. (1987) Pharmacology and pharmacokinetics of estrogens. American Journal of Obstetrics and Gynecology vol. 156, pp. 1289–1293.
2. Stumpf, P. G. (1990) Pharmacokinetics of estrogen. Obstetrics and Gynecology vol. 75 (suppl.), pp 9S–14S.
3. Marsh, M. S. and Whitehead, M. I. (1992) Management of the menopause. British Medical Bulletin vol. 48, pp. 426–457.
4. Place, V. A. et al. (1985) A double-blind comparative study of Estraderm and Premarin in the amelioration of postmenopausal symptoms. American Journal of Obstetrics and Gynecology vol. 152, pp. 1092–1099.
5. Kuhl, H. (1990) Pharmacokinetics of oestrogens and progestogens. Maturitas vol. 12, pp. 171–197.
6. Chien, Y. W. (1992) Vaginal Drug Delivery and Delivery Systems. In: Novel Drug Delivery Systems, 2nd edn. Marcel Dekker, New York, pp. 529–584.
7. Rigg, L. A. et al. (1978) Absorption of estrogens from vaginal creams. New England Journal of Medicine vol. 298, pp. 195–197.
8. Jackanicz, T. M. (1979) Vaginal ring steroid-releasing systems. In Long-Acting Contraceptive Delivery Systems (Zatuchni, G. I. et al., eds.). Harrow and Row, Philadelphia, pp. 201–212.
9. Englund, D. E. et al. (1981) Pharmacokinetics and pharmacodynamic effects of vaginal oestradiol administration from silastic rings in postmenopausal women. Maturitas vol. 3, pp. 125–133.
10. Roy, S. and Mishell, D. R. (1983) Vaginal ring clinical studies: update. In: Long-Acting Contraceptive Delivery Systems (Zatuchni, G. I. et al., eds.). Harrow and Row, Philadelphia, pp. 581–594.
11. Stumpf, P. G. et al. (1982) Development of a vaginal ring for achieving physiologic levels of 17β-estradiol in hypoestrogenic women. Journal of Clinical Endocrinology and Metabolism vol. 54, pp. 208–210.
12. Stumpf, P. G. (1986) Selecting constant serum estradiol levels achieved by vaginal rings. Obstetrics and Gynecology vol. 67, pp. 91–94.
13. Smith, P. et al. (1993) Oestradiol-releasing vaginal ring for treatment of postmenopausal urogenital atrophy. Maturitas vol. 16, pp. 145–154.

I claim:

1. A cylindrical intravaginal drug delivery device suitable for administration to a female mammal, the device comprising a 17β-oestradiol precursor in a biocompatible hydrophobic elastomeric polymer matrix, the device releasing the 17β-oestradiol precursor in a substantially zero order pattern for at least three weeks, the precursor being a 17β-oestradiol moiety in which the, or each, hydroxyl group of the 17β-oestradiol moiety is blocked by a blocking group, the precursor having sufficient lipophilicity as determined either by a solubility in liquid silicone of not less than 0.1 mg/100 ml or by a standard k value, in which k=$2C_S D\pi$, of not less than 0.1 μg/day/mm, the precursor having sufficient hydrophilicity as determined by a solubility in distilled water of not less than 1 μg/100 ml, the, or each, blocking group being so linked to the 17β-oestradiol moiety as to be readily removed from the 17β-oestradiol moiety in vivo, and the, or each, blocking group being so chosen as to yield a substance which is non-toxic to the female mammal when removed from the 17β-oestradiol moiety in vivo wherein $C_S$ corresponds to the precursor's saturation solubility in the polymer matrix and D corresponds to the precursor's diffusion coefficient in the polymer matrix.

2. An intravaginal drug delivery device according to claim 1, in which the, or each, blocking group is an aliphatic $C_{1-5}$ acyl group, with the proviso that, when the acyl group is acetyl, each hydroxyl group cannot be blocked with acetyl.

3. An intravaginal drug delivery device according to claim 2, in which the acyl group is the acyl moiety of a saturated monocarboxylic or dicarboxylic acid.

4. An intravaginal drug delivery device according to claim 3, in which the acyl group is selected from the group comprising formyl, acetyl, propionyl, butyryl, isobutyryl, oxalyl, malonyl, succinyl and glutaryl.

5. An intravaginal drug delivery device according to claim 2, in which the acyl group is the acyl moiety of an unsaturated monocarboxylic or dicarboxylic acid.

6. An intravaginal drug delivery device according to claim 5, in which the acyl group is selected from acryloyl, propioloyl, methacryloyl, crotonoyl, isocrotonoyl, maleoyl, fumaroyl, citraconoyl and mesaconoyl.

7. An intravaginal drug delivery device according to claim 1, in which the blocking group blocks the 3-hydroxyl group of the 17β-oestradiol moiety.

8. An intravaginal drug delivery device according to claim 1, in which the blocking group blocks the 17-hydroxyl group of the 17β-oestradiol moiety.

9. An intravaginal drug delivery device according to claim 7, in which the blocking group is selected from acetyl or propionyl.

10. An intravaginal drug delivery device according to claim 7, in which the precursor is 17β-oestradiol-3-acetate or 17β-oestradiol-3-propionate.

11. An intravaginal drug delivery device according to claim 8, in which the precursor is 17β-oestradiol-17-acetate or 17β-oestradiol-17-propionate.

12. An intravaginal drug delivery device according to claim 1, in which the device additionally includes a progestogen in the polymer matrix.

13. An intravaginal drug delivery device according to claim 12, in which the progestogen is selected from the group comprising norethisterone-17-acetate and levonorgestrel.

14. An intravaginal drug delivery device according to claim 1 suitable for inducing hyper-oestrogenism including fertility control, in which the polymer matrix forms a hollow annulus and the device is provided with a central member within the annulus and a sheath surrounding the polymer matrix.

15. A process for the preparation of a cylindrical intravaginal drug delivery device for release in a substantially zero order pattern for at least three weeks and suitable for administration to a female mammal, the process comprising the steps of:

combining a 17β-oestradiol precursor, the precursor being a 17β-oestradiol moiety in which the, or each, hydroxyl group of the 17β-oestradiol moiety is blocked by a blocking group; the precursor having sufficient lipophilicity as determined either by a solubility in liquid silicone of not less than 0.1 mg/100 ml or by standard k value as defined hereinabove of not less than 0.1 μg/day/mm, the precursor having sufficient hydrophilicity as determined by a solubility in distilled water of not less than 1 μg/100 ml, the, or each, blocking group being so linked to the 17β-oestradiol moiety as to be readily removed from the 17β-oestradiol moiety in vivo; and the, or each, blocking group being so chosen as to yield a substance which is non-toxic to the female mammal, when removed from the 17β-oestradiol moiety in vivo, with a biocompatible hydrophobic elastomeric polymer, a suitable cross-linking agent and a curing catalyst to form a mix; and curing the mix to form a polymer matrix.

16. A process according to claim 15, in which the polymer matrix forms a hollow annulus and the process comprises the steps of forming a central member; combining the 17β-oestradiol precursor with a polymer, a suitable cross-linking agent and a curing catalyst to form a mix and curing the mix to form the polymer matrix in the form of the hollow annulus surrounding the central member; and providing a sheath surrounding the polymer matrix.

17. An intravaginal drug delivery device suitable for administration to a female mammal, whenever prepared by the process claimed in claim 15.

18. A method of using a 17β-oestradiol precursor in a cylindrical intravaginal drug delivery device for release in a substantially zero order pattern for at least three weeks, which method comprises the step of incorporating in the drug delivery device the 17β-oestradiol precursor, wherein the 17β-oestradiol precursor is a 17β-oestradiol moiety in which the, or each, hydroxyl group of the 17β-oestradiol moiety is blocked by a blocking group, the precursor has sufficient lipophilicity as determined either by a solubility in liquid silicone of not less than 0.1 mg/100 ml or by a standard k value as defined hereinabove of not less than 0.1 μg/day/mm, the precursor has sufficient hydrophilicity as determined by a solubility in distilled water of not less than 1 μg/100 ml, the, or each, blocking group is so linked to the 17β-oestradiol moiety as to be readily removed from the 17β-oestradiol moiety in vivo, and the, or each, blocking group is so chosen as to yield a substance which is non-toxic to the female mammal when removed from the 17β-oestradiol moiety in vivo.

19. A method of releasing a 17β-oestradiol precursor in a substantially zero order pattern for a least three weeks, which method comprises the steps of:

incorporating the 17β-oestradiol precursor in a cylindrical intravaginal drug delivery device, the 17β-oestradiol precursor being a 17β-oestradiol moiety in which the, or each, hydroxyl group of the 17β-oestradiol moiety is blocked by a blocking group, the precursor having sufficient lipophilicity as determined either by a solubility in liquid silicone of not less than 0.1 mg/100 ml or by a standard k value as defined hereinabove of not less than 0.1 μg/100 ml, the precursor having sufficient hydrophilicity, as determined by a solubility in distilled water or not less than 1 μg/100 ml, the, or each, blocking group being so linked to the 17β-oestradiol moiety as to be readily removed from the 17β-oestradiol moiety in vivo, the, or each, blocking group being so chosen as to yield a substance which is non-toxic to the female mammal when removed from the 17β-oestradiol moiety in vivo; and inserting the drug delivery device into a vagina of a female mammal for the at least three weeks.

20. An intravaginal drug delivery device according to claim 1 suitable for alleviating or preventing symptoms associated with hypo-oestrogenism including hormone replacement therapy, in which the polymer matrix forms a core and the device is provided with a sheath surrounding the polymer matrix.

21. A process according to claim 15, in which the polymer matrix forms a core and the process additionally comprises the step of providing a sheath surrounding the polymer matrix.

22. An intravaginal drug delivery device suitable for administration to a female mammal, whenever prepared by the process claimed in claim 16.

23. An intravaginal drug delivery device according to claim 10, in which the precursor is 17β-oestradiol-3-acetate.

24. An intravaginal drug delivery device according to claim 11, in which the precursor is 17β-oestradiol-17-acetate.

* * * * *